United States Patent
Smith et al.

(10) Patent No.: US 6,652,570 B2
(45) Date of Patent: *Nov. 25, 2003

(54) COMPOSITE VASCULAR GRAFT

(75) Inventors: Scott Smith, Chaska, MN (US); Christopher Brian Brodeur, Blaine, MN (US)

(73) Assignee: SciMed Life Systems, Inc., Maple Grove, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,218

(22) Filed: Jul. 2, 1999

(65) Prior Publication Data

US 2001/0023370 A1 Sep. 20, 2001

(51) Int. Cl.[7] .................................................. A61F 2/06
(52) U.S. Cl. ..................................... 623/1.13; 623/1.32
(58) Field of Search ................................ 606/108, 192, 606/194, 195, 198; 623/1, 1.13, 1.14, 1.32, 1.33

(56) References Cited

U.S. PATENT DOCUMENTS

| | | |
|---|---|---|
| 4,925,710 A | 5/1990 | Buck et al. |
| 5,123,917 A | 6/1992 | Lee |
| 5,282,824 A | 2/1994 | Gianturco |
| 5,389,106 A | 2/1995 | Tower |
| 5,466,509 A | 11/1995 | Kowligi et al. |
| 5,507,771 A | 4/1996 | Gianturco |
| 5,562,697 A | 10/1996 | Christiansen |
| 5,562,728 A | 10/1996 | Lazarus et al. |
| 5,591,195 A | 1/1997 | Taheri et al. |
| 5,607,478 A | 3/1997 | Lentz et al. |
| 5,620,763 A | 4/1997 | House et al. |
| 5,641,373 A | 6/1997 | Shannon et al. |
| 5,653,697 A | 8/1997 | Quiachon et al. |
| 5,674,241 A | 10/1997 | Bley et al. |
| 5,700,285 A | 12/1997 | Myers et al. |
| 5,713,917 A | 2/1998 | Leonhardt et al. |
| 5,718,973 A | 2/1998 | Lewis et al. |
| 5,735,892 A | 4/1998 | Myers et al. |
| 5,749,880 A | 5/1998 | Banas et al. |
| 5,810,870 A | 9/1998 | Myers et al. |
| 5,824,037 A | 10/1998 | Fogarty et al. |
| 5,843,173 A | 12/1998 | Shannon et al. |
| 5,897,587 A | 4/1999 | Martakos et al. |
| 5,910,168 A | 6/1999 | Myers et al. |
| 5,928,279 A * | 7/1999 | Shannon et al. ............... 623/1 |
| 6,042,605 A * | 3/2000 | Martin et al. .................. 623/1 |
| 6,264,684 B1 * | 7/2001 | Banas et al. ............... 623/1.13 |

FOREIGN PATENT DOCUMENTS

| | | |
|---|---|---|
| DE | 195 31 659 A1 | 3/1997 |
| EP | 0 792 627 A2 | 9/1997 |
| EP | 0 893 108 A2 | 1/1999 |
| WO | WO 95/05132 | 2/1995 |
| WO | WO 95/05555 | 2/1995 |
| WO | WO 96/28115 | 9/1996 |
| WO | WO 98/00090 | 1/1998 |
| WO | WO 98/27894 | 2/1998 |
| WO | WO 98/27893 | 7/1998 |
| WO | WO 00/45741 | 8/2000 |
| WO | WO 00/45742 | 8/2000 |
| WO | WO 00/45743 | 8/2000 |

* cited by examiner

Primary Examiner—Michael H. Thaler
(74) Attorney, Agent, or Firm—Hoffman & Baron, LLP

(57) ABSTRACT

A composite stent/graft tubular prosthesis includes an inner PTFE tubular structure, an outer PTFE tubular structure assembled about the inner PTFE tubular structure, and a circumferentially distensible stent interposed between the inner and outer PTFE tubular structures. The outer tubular body is a non-continuous body formed of polytetrafluoroethylene components, providing axial and circumferential compliance to said prosthesis. The outer tubular body completely overlies the distensible stent.

3 Claims, 6 Drawing Sheets

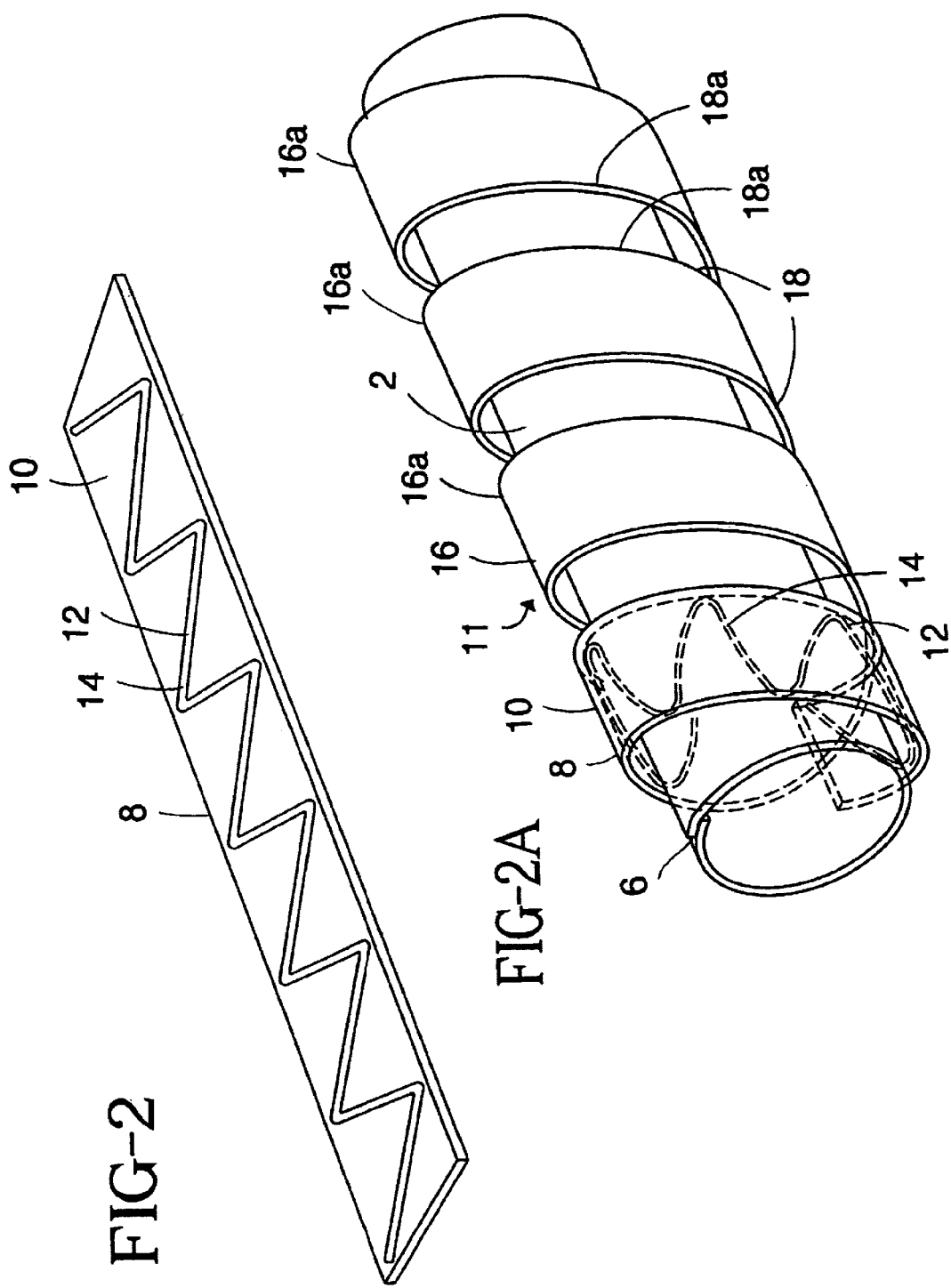

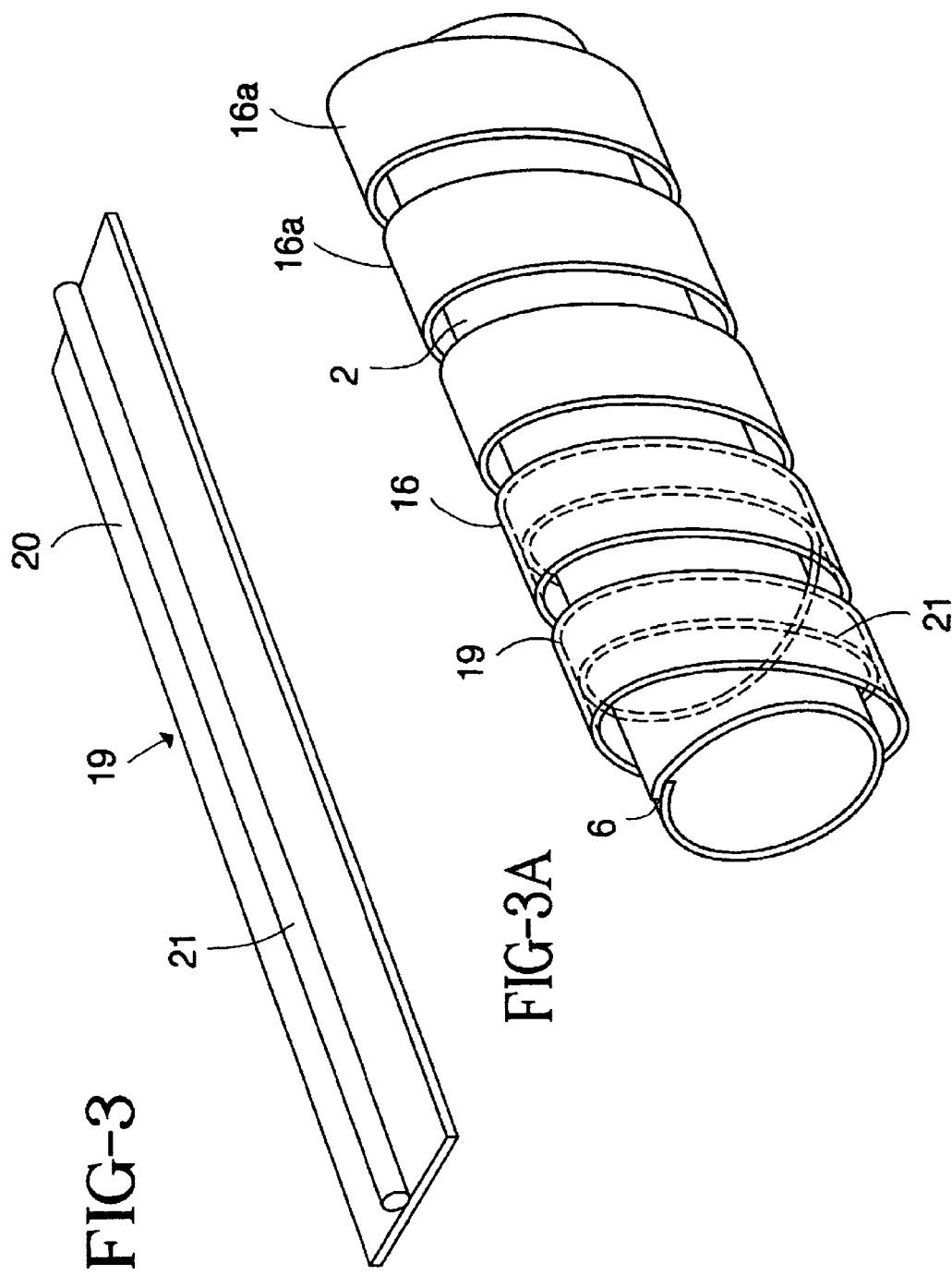

COMPOSITE VASCULAR GRAFT

FIELD OF THE INVENTION

The present invention relates generally to a tubular implantable prosthesis formed of porous expanded polytetrafluoroethylene. More particularly, the present invention relates to a composite, multi-layered endoprosthesis having increased axial and radial compliance.

BACKGROUND OF THE INVENTION

An intraluminal prosthesis is a medical device commonly known to be used in the treatment of diseased blood vessels. An intraluminal prosthesis is typically used to repair, replace, or otherwise correct a damaged blood vessel. An artery or vein may be diseased in a variety of different ways. The prosthesis may therefore be used to prevent or treat a wide variety of defects such as stenosis of the vessel, thrombosis, occlusion, or an aneurysm.

One type of endoluminal prosthesis used in the repair of diseases in various body vessels is a stent. A stent is a generally longitudinal tubular device formed of biocompatible material which is useful to open and support various lumens in the body. For example, stents may used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpended insertion diameter and an expanded implantation diameter which is greater than the unexpended insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of commonly known type of intraluminal prosthesis which is used to repair and replace various body vessels. A graft provides an artificial lumen through which blood may flow. Grafts are tubular devices which may be formed of a variety of material, including textiles, and non-textile materials. One type of non-textile material particularly useful as an implantable intraluminal prosthesis is polytetrafluoroethylene (PTFE). PTFE exhibits superior biocompatability and low thrombogenicity, which makes it particularly useful as vascular graft material in the repair or replacement of blood vessels. In vascular applications, the grafts are manufactured from expanded polytetrafluoroethylene (ePTFE) tubes. These tubes have a microporous structure which allows natural tissue ingrowth and cell endothelization once implanted in the vascular system. This contributes to long term healing and patency of the graft. These tubes may be formed from extruded tubes or may be formed from a sheet of films formed into tubes.

Grafts formed of ePTFE have a fibrous state which is defined by interspaced nodes interconnected by elongated fibrils. The spaces between the node surfaces that is spanned by the fibrils is defined as the internodal distance (IND). Porosity of a graft is measured generally by IND. In order of proper tissue ingrowth and cell endothelization, grafts must have sufficient porosity obtained through expansion. When the term expanded is used to describe PTFE, it is intended to describe PTFE which has been stretched, in accordance with techniques which increase IND and concomitantly porosity. The stretching may be in uni-axially, bi-axially, or multi-axially. The nodes are spaced apart by the stretched fibrils in the direction of the expansion. Properties such as tensile strength, tear strength and radial (hoop) strength are all dependent on the expansion process. Expanding the film by stretching it in two directions that are substantially perpendicular to each other, for example longitudinally and transversely, creates a biaxially oriented material. Films having multi-axially-oriented fibrils may also be made by expanding the film in more than two directions. Porous ePTFE grafts have their greatest strength in directions parallel to the orientation of their fibrils. With the increased strength, however, often comes reduced flexibility.

While ePTFE has been described above as having desirable biocompatability qualities, tubes comprised of ePTFE, as well as films made into tubes, tend to exhibit axial stiffness, and minimal radial compliance. Longitudinal compliance is of particular importance to intraluminal prosthesis as the device must be delivered through tortuous pathways of a blood vessel to the implantation site where it is expanded. A reduction in axial and radial flexibility makes intraluminal delivery more difficult.

Composite intraluminal prosthesis are known in the art. In particular, it is known to combine a stent and a graft to form a composite medical device. Such composite medical devices provide additional support for blood flow through weakened sections of a blood vessel. In endovascular applications the use of a composite graft or a stent/graft combination is becoming increasingly important because the combination not only effectively allows the passage of blood therethrough, but also ensures patency of the implant. But, composite prosthesis, especially those consisting of ePTFE, while exhibiting superior biocompatability qualities, also exhibit decreased axial and radial compliance. It is therefore desirable to provide an ePTFE composite intraluminal prosthesis which exhibits increased axial and radial compliance.

SUMMARY OF THE INVENTION

The present invention comprises a composite ePTFE vascular prosthesis. The composite has three layers; an inner tubular ePTFE layer, a discontinuous outer layer, and a radially deformable stent atop the inner tubular layer and entirely beneath the outer layer.

One advantage of the present invention is that it provides an improved composite ePTFE intraluminal prosthesis exhibiting increased axial and circumferential compliance and flexibility and greater tissue ingrowth.

Another advantage of the present invention is that it provides an improved stent/graft combination, exhibiting increased axial and circumferential compliance and flexibility.

Another advantage of the present invention is that it provides an improved composite ePTFE intraluminal prosthesis exhibiting increased axial and circumferential compliance and flexibility and greater tissue ingrowth through the use of multiaxial fibril direction in a non-continuous outer ePTFE tubular body.

It is yet another advantage of the present invention to provide an improved method of forming such composites using preassembled graft/stent strips.

The present invention provides a composite intraluminal prosthesis for implantation which may have a substantially continuous ePTFE tubular inner body in combination with a non-continuous outer ePTFE tubular body formed by tubularly assembled polytetrafluoroethylene strips, or components. A circumferentially distensible support structure is interposed between the two PTFE layers. The components or strips comprising the outer tubular body possess a longitudinal length and a width, with said longitudinal length being greater than said widths; the non-continuous, tubular assembled strips providing axial and circumferential compliance to said prosthesis.

A method of forming an intraluminal prosthesis stent/graft with axial and circumferential compliance is provided by combining a non-continuous PTFE tubular outer body over a substantially continuous PTFE tubular inner body, said outer body and inner body supporting a stent thereinbetween. Use of a braided or woven PTFE in at least the outer layer enhances the axial and circumferential compliance, and provides puncture sealing properties to prosthesis of the present invention.

BRIEF DESCRIPTION OF THE DRAWINGS

FIG. 2 is a perspective view of an assembly strip of the present invention, including a planar graft strip and an undulating wire stent, for forming a composite stent/graft prosthesis according to the present invention.

FIG. 2A is a perspective showing, partially in section of a portion, of the composite stent/graft prosthesis of the present invention.

FIG. 3 is a perspective view of an assembly strip of the present invention, including a planar graft strip and a substantially linear wire stent, for forming the composite stent graft prosthesis according to the present invention.

FIG. 3A is a perspective showing of a portion of a composite stent/graft prosthesis of the present invention.

DETAILED DESCRIPTION OF THE INVENTION

The prosthesis of the preferred embodiment of the present invention is a composite implantable intraluminal prosthesis which is particularly suited for use as a vascular graft. The composite prosthesis of the present invention includes a multi-layer graft structure with radially deformable stent interposed between layers. The present description is meant to describe the preferred embodiments, and is not meant to limit the invention in any way.

Figure 1:
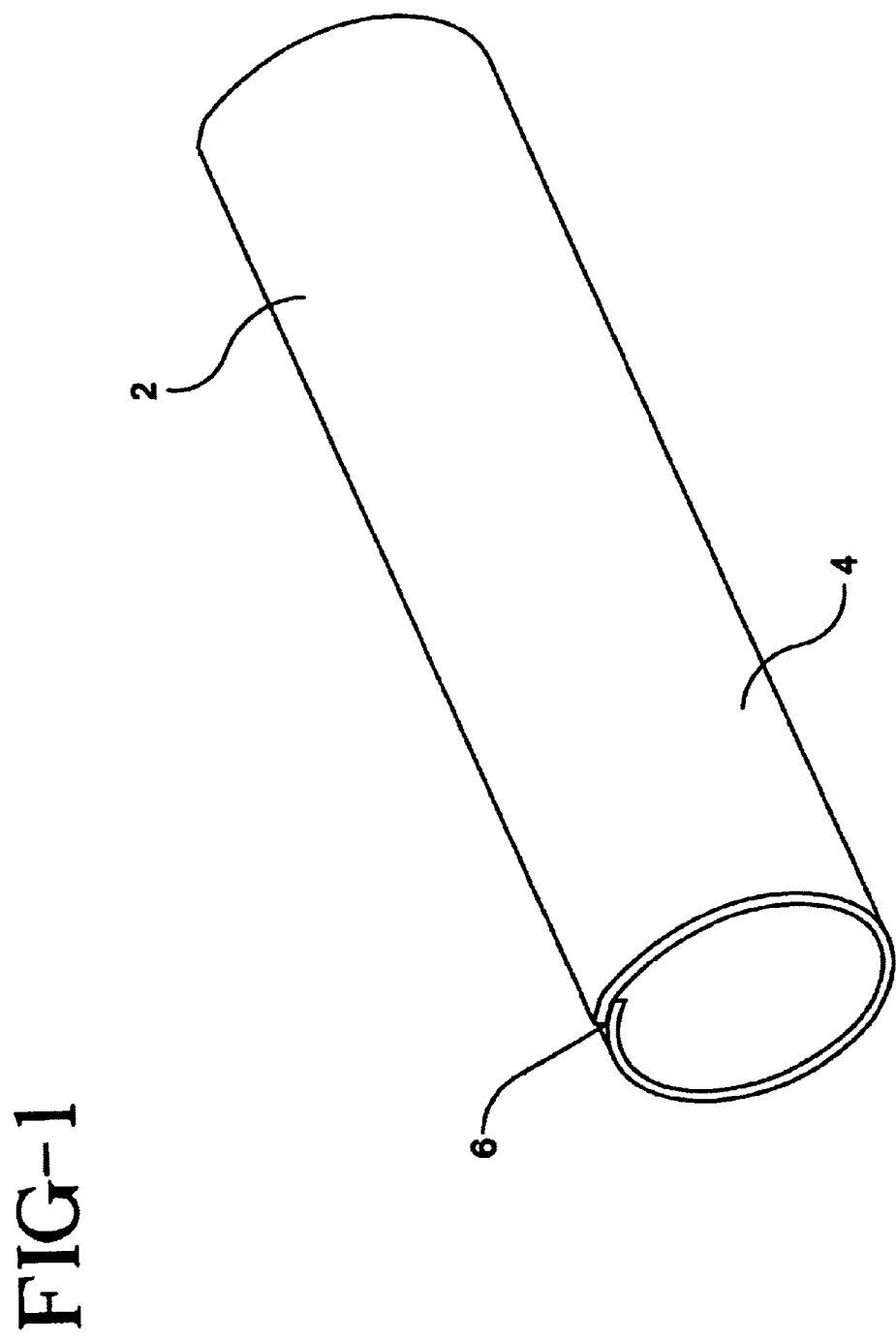
FIG. 1 is a perspective showing of a tubular structure which may be used as the inner tubular structure of the prosthesis of the present invention.

Shown in FIG. 1 is a continuous tubular inner PTFE body 2 which may form one of the layers of the multilayer graft. The braided tubular body is formed by wrapping a PTFE sheet 4 around a mandrel (not shown), to form a tubular body with a seam 6 longitudinally therealong. The seam in the tube may be bonded thermally, adhesively, or with the use of a polymeric solution. It may be fully or partially bonded. Furthermore, the tube may consist of one single layer of the wrap as shown in FIG. 1, or it may consist of multiple windings of the PTFE sheet around the longitudinal axial to create a multi-layer inner tube.

While in the preferred embodiment, tubular body 2 is formed from a wrapped PTFE sheet, tubes of extruded PTFE may be used to form the continuous inner tubular body of the present invention.

Continuous, as used herein, refers to a tubular structure whose surface extends substantially uninterrupted throughout the longitudinal length thereof. In the case of an extruded tube, the tubular structure is completely uninterrupted. In the case of a sheet formed tube there are no transverse interruptions. As is known in the art, a substantially uninterrupted tubular structure exhibits enhanced strength and sealing properties when used as a vascular graft.

Figure 2B:
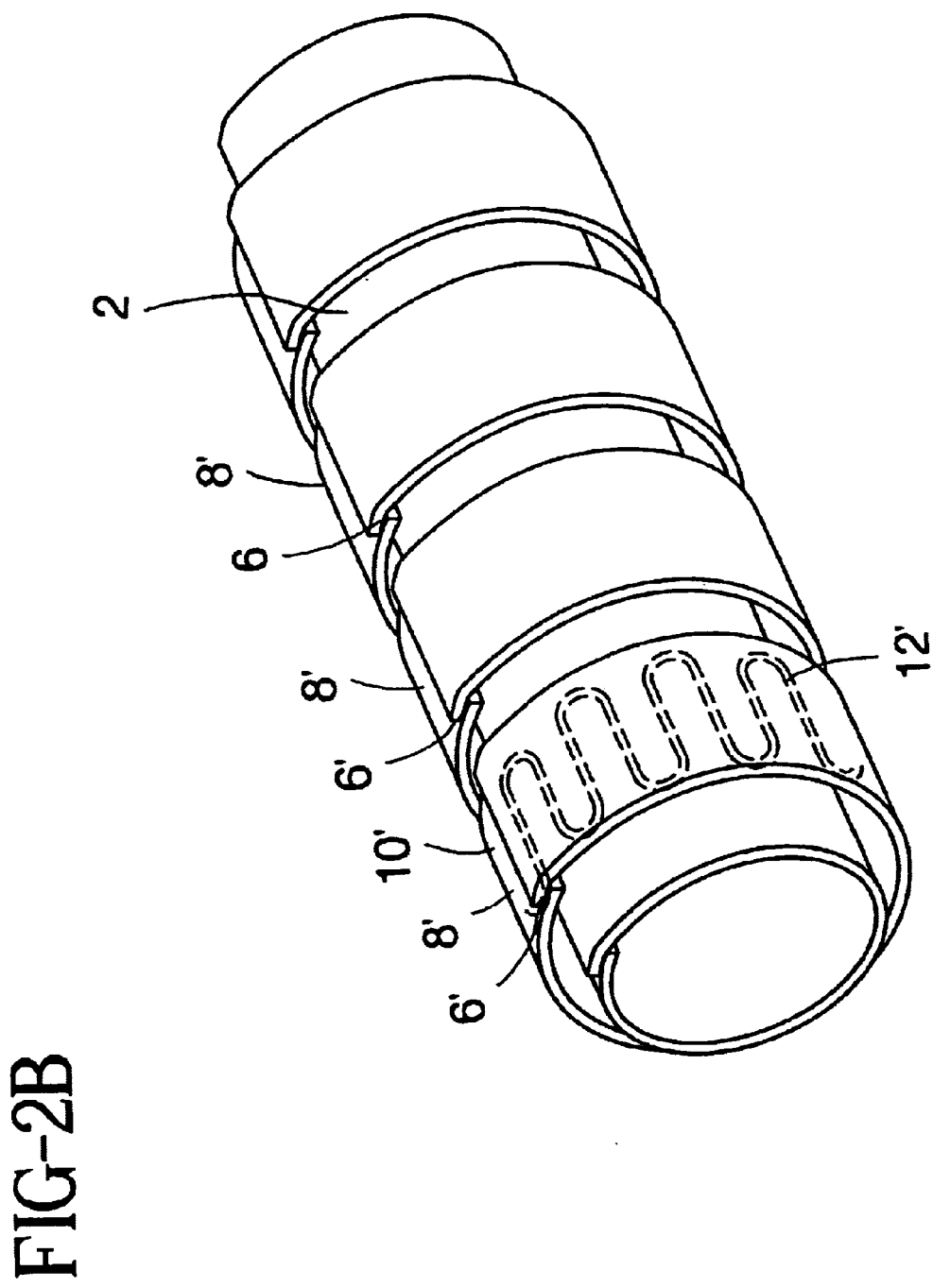
FIG. 2B is a perspective showing of another stent/graft composite prosthesis of the present invention.

FIG. 2 depicts an assembly strip 8 for forming a composite stent/graft prosthesis 11 according to the present invention. The assembly strip 8 comprises a planar graft strip 10 and a radially deformable support structure such as planar stent 12 in this embodiment, an undulating wire stent 14. Distensible, as used herein, refers to a stent which may be expanded and contracted radially. The stent 12 may be temporarily fastened to the strip, or simply assembled therewith. The composite prosthesis 11 is made by wrapping the assembly strip about a tubular inner PTFE body 2, and securing the graft strip directly to the tubular graft body. As shown in FIG. 2A, preferably the strip is wound helically around the tubular inner body 2. One preferred construction for assembly strip 8 is shown and described in commonly assigned U.S. patent application, entitled "Helically Formed Stent/Graft Assembly" and filed at even date herewith. This application is incorporated by reference herein. In an alternate construction depicted in FIG. 2B, individual assembly strips, 8', are joined at seams 6' in an annular fashion to form a plurality of spaced apart stent/graft covers over tubular body 2.

As shown in the drawings, particularly FIGS. 2, 2A and 2B, the strip 8 is applied in such a manner that the wire stent 14 is disposed in direct contact with the inner tubular 2. This forms a low profile configuration of a stent positioned directly between single layers of PTFE material.

Various stent types and stent constructions may be employed in the invention. Among the various stents useful include, without limitation, self-expanding stents and balloon expandable extents. The stents may be capable of radially contracting, as well, and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other bicompatible metals, as well as polymeric stents.

The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

In constructing the composite intraluminal prosthesis 11 of FIG. 2A, it is not necessary to preassemble strips 8. In one method of construction, the inner tubular body 2 is circumferentially enclosed by stent 12. The stent 12 may be formed from an elongate wire 14 which is helically wound with a plurality of longitudinally spaced turns into an open tubular configuration. The stent may be of the type described in U.S. Pat. No. 5,575,816 to Rudnick, et al. Stent 12 is an expandable tubular member which may be either of the balloon-expanded or self-expanded type. Stents of this type are typically introduced intraluminally into the body, and expanded at the implantation site.

The composite endoluminal prosthesis 11 is completed by wrapping strip(s) of ePTFE over the stent, to make a non-continuous outer PTFE tubular body 16 which circumferentially surrounds the inner tube 2 and the stent 12. Non-continuous, as used herein, refers to a tubular structure which is not substantially uninterrupted along its length as it contains at least two spaced apart edges 18 and 18a transverse to the longitudinal surface of the tubular body. The non-continuous outer PTFE tubular body 16 is comprised of a flat PTFE tape helically wound around the inner tube 2 and stent 12 so as to completely overly the stent.

The outer body 16 possesses edges 18 which define the separate PTFE components, and edges 18a define open spaced in the outer PTFE tubular body 16. The PTFE components shown in outer tube 16 consist of the successively spaced helical turns 16a of an axially wrapped PTFE tape 10. Prior to winding, the PTFE tape 10 has a substantially flat cross-section, and a longitudinal length substantially longer than the width of the tape.

Referring now to FIG. 2B, the composite endoluminal prosthesis may be alternatively constructed by winding individual stent sections 12' axially about tube 2, and overlying the stent sections with strips 10', or cutting preassembled strip sections 8' and seaming them at 6'. The embodiment of FIG. 2B is also non-continuous defining spaced apart edges 18 identifying open spaces therebetween.

FIG. 3 shows an alternate assembly strip construction 19 comprising a planar graft strip 20 assembly with a stent 21, which in this embodiment is a substantially straight wire. In assembling a composite endoluminal prosthesis from assembly strip 19, the strip may be helically wound in a non-overlapping configuration about inner tubular member 2 in a manner similar to that described with respect to FIG. 2A. Tape 20 may be secured to inner tubular body 2, sealing the stent within the composite. Alternatively, the stent may be wound about the inner tubular member, and graft strip 20 laid atop the stent. It should also be noted that assembly strip 19 may be cut into segments, each of which may be wound circumferentially about the tube body 2, and seamed in a manner similar to that described with respect to FIG. 2B.

Figure 4:
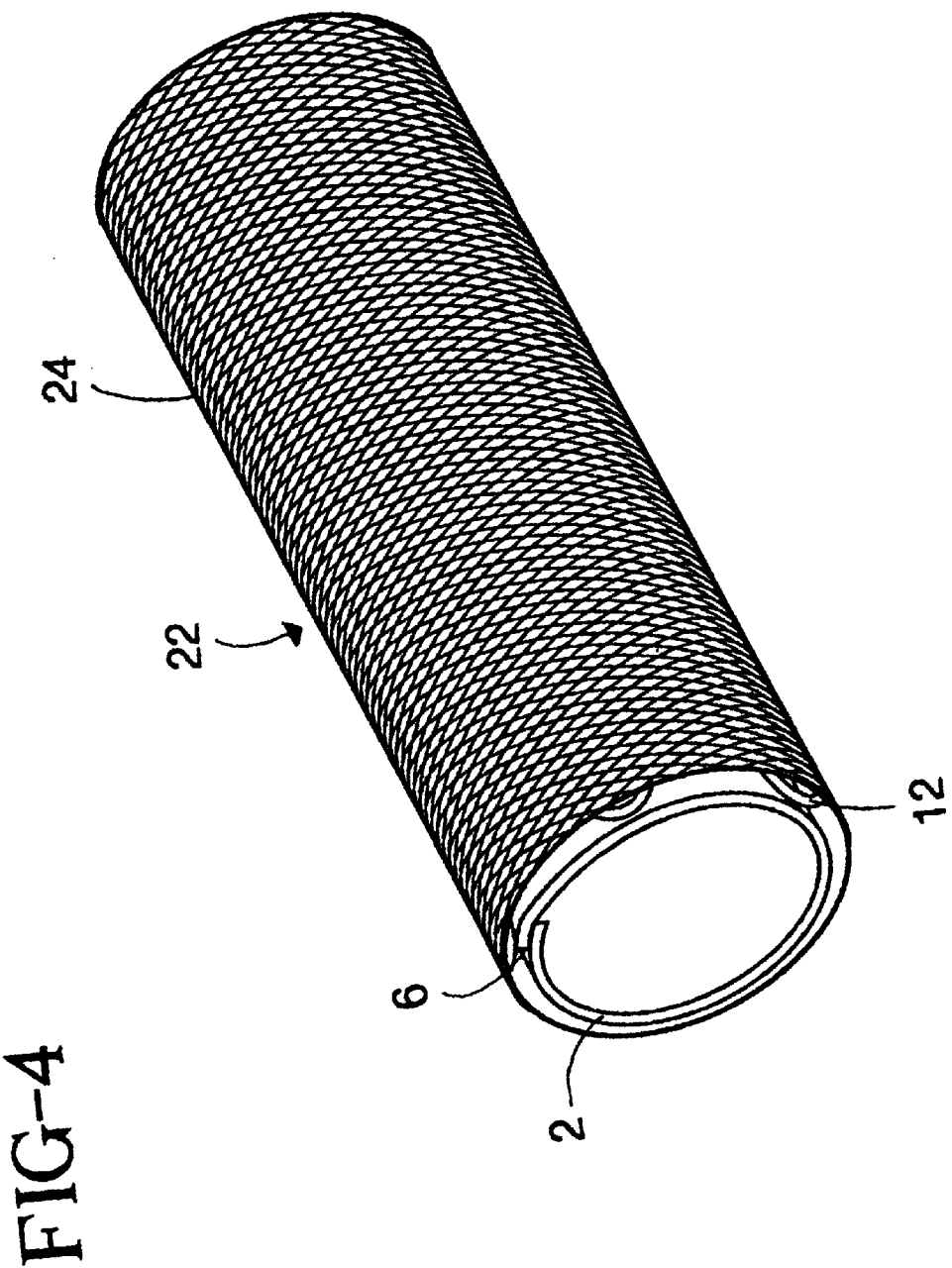
FIG. 4 shows a partial perspective of the stent and exterior surface of the outer PTFE tubular body of another embodiment of the present invention.

FIG. 4 depicts a further embodiment of the present invention which also provides a non-continuous outer tube. This embodiment employs an inner tube 2 and a stent 12 as described above in relation to FIGS. 2 and 2A. In this preferred embodiment, the composite prosthesis 22 possesses an outer tubular body 24 including a weave, or a braid of individual PTFE tapes. The woven or braided configuration may be two dimensional or may be three dimensional, as shown in FIGS. 5 and 6.

Figure 5:
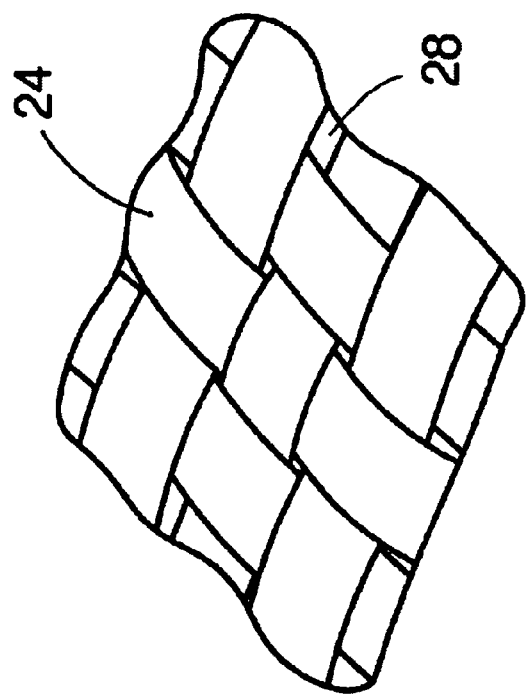
FIG. 5 shows an enlarged perspective view of the exterior surface of another embodiment of the outer PTFE tubular body.

FIG. 5 shows two PTFE tapes combined in a two dimensional matrix, wherein the two tapes comprise the separate components of the non-continuous tubular body 24.

Figure 6:
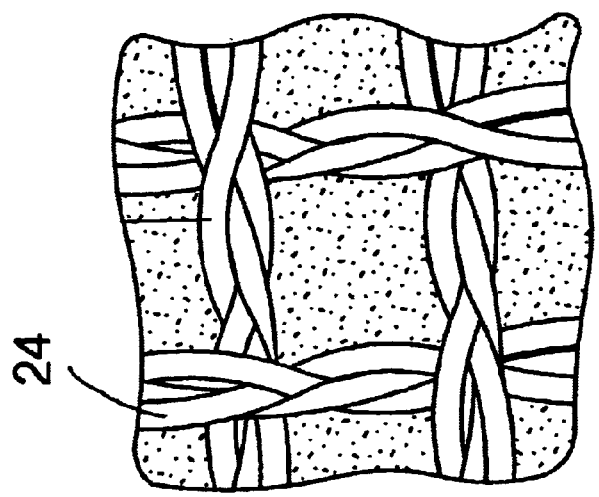
FIG. 6 shows an enlarged perspective of the exterior surface of another embodiment of the outer PTFE tubular body.

FIG. 6 shows an enlarged view of a three dimensional braid comprised of three PTFE tapes braided together in three directions. Such braided, knitted or woven construction provides axial and radial compliance to the prosthesis 22 by defining spaces within the braided, knitted or woven extruded structure.

In certain applications where enhanced sealing properties are required, a sealant 28, as shown in FIG. 6, may be interspersed within the woven or braided matrix to create a non-porous outer tubular body. Sealants which may be used in the prosthesis include FEP, polyurethane, and silicone. Additional sealants include biological materials such as collagen, and hydrogels, polymethylmethacrylate, polyamide, and polycarbonate. Elastomers as sealants will have less impact on flexibility. A suitable sealant provides a substantially sealed outer tube without significantly reducing longitudinal and axial compliance.

As shown herein the outer tubular body shown in the above-referenced figures form non-continuous bodies comprised of PTFE components tubularly assembled. The non-continuous structure of the outer tubular body provides the composite prosthesis with enhanced radial and longitudinal, or axial compliance. The radial and axial compliance can, in fact, be varied with the different outer PTFE bodies which may be used, as may be suitable for the use of the intraluminal prosthesis. The non-continuous outer layer 16 is formed by wrapping one, two, or three or more PTFE tapes in an axial wrap, weave, braid or other non-continuous tubular body consisting of the component PTFE parts defined above.

In preferred embodiments the PTFE tape forming the PTFE components is expanded PTFE (ePTFE). The term expanded refers to PTFE which has been stretched uniaxially, biaxially, or multiaxially in a particular direction. The PTFE tape of the prosthesis of the present invention is typically stretched in the longitudinal direction of the tape. When two or more tapes are combined to form the outer tubular body, the resultant tubular body possesses a biaxial, or multiaxial resultant orientation in the aggregate. Because ePTFE exhibits increased strength in the direction of its stretching, the ePTFE tubularly assembled body exhibits the advantage of the increased strength of a biaxial or multiaxial stretched film, but exhibits the advantages of compliance because of its non-continuous surface.

The inner PTFE tubular layer may be bonded to the outer PTFE tubular layer through spaces in the open wall of the stent. The bonding may be effectuated with the use of an adhesive, or by adhering the layers together without an adhesive. Bonding of the PTFE layers without an adhesive may take place by such methods as laminating, or sintering of the prosthesis. Furthermore, the stent may be adhered to the inner PTFE tubular layer, the outer PTFE tubular layer, or both. Similarly, such adherence may take place with or without the use of an adhesive.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable composite intraluminal prosthesis comprising:

a continuous, uninterrupted polytetrafluoroethylene tubular inner body, having a cross-section which is uniform through out its entire length;

a longitudinally non-continuous outer tubular body; and an open wall stent applied in direct contact with said inner body and interposed between the inner and outer tubular bodies, said outer tubular body being formed of polytetrafluoroethylene tape segments, having a longitudinal length and a width, said longitudinal length being greater than said width, said segments circumferentially surrounding and completely overlying said stent and bonded to said tubular inner body through said open wall of said stent, whereby axial and circumferential compliance is provided to said prosthesis.

2. A composite intraluminal prosthesis according to claim 1 wherein the outer polytetrafluoroethylene body comprises a polytetrafluoroethylene tape spirally wrapped with a plurality of helical turns in a circumferential direction around the inner tubular body and said stent, wherein each helical turn of said spiral wrap defines one of said polytetrafluoroethylene segments.

3. A composite intraluminal prosthesis according to claim 1 wherein said continuous polytetrafluoroethylene tubular inner body is comprised of a sheet of expanded polytetrafluoroethylene formed into a tubular shape by wrapping said sheet about a longitudinal axis.

* * * * *